United States Patent [19]

Blüethgen et al.

[11] 4,131,597
[45] Dec. 26, 1978

[54] BIOACTIVE COMPOSITE MATERIAL PROCESS OF PRODUCING AND METHOD OF USING SAME

[75] Inventors: Waldemar Blüethgen, Braunsfels; Heinz Bröemer, Hermannstein; Klaus K. Deutscher, Wetzlar, all of Germany

[73] Assignee: Ernst Leitz GmbH, Wetzlar, Germany

[21] Appl. No.: 648,505

[22] Filed: Jan. 12, 1976

[30] Foreign Application Priority Data

Jan. 17, 1975 [DE] Fed. Rep. of Germany ....... 2501683

[51] Int. Cl.$^2$ .............................................. C08K 7/14
[52] U.S. Cl. ..................................... 260/42.18; 3/1.9; 32/8; 32/10 A; 106/35; 128/92 C; 260/42.52
[58] Field of Search ............ 106/35; 260/42.18, 42.52; 3/1.9; 32/8, 10 A; 128/92 C

[56] References Cited

U.S. PATENT DOCUMENTS

| 3,860,556 | 1/1975 | Taylor | 260/42.52 |
| 3,922,155 | 11/1975 | Broemer et al. | 106/47 R |
| 3,923,740 | 12/1975 | Schmitt et al. | 260/42.18 |
| 3,968,073 | 7/1976 | Hara et al. | 260/42.18 |

OTHER PUBLICATIONS

Blencke et al., Compatibility and Long Term Stability of Glass–Ceramic Inplants (10 pages), paper presented at the 8th International Biomaterials Symposium at Philadelphia, 1976.
Hennig et al., "Investigations with Bioactivated Polymethylmethacrylates," Apr. 28, 1978 (8 pages).
Tissue Reactions after Hip Joint Replacement Experimental Results with Bioactivated Bone Cement (7 pages), Apr. 28, 1978.
Blencke et al., "Glaskeramiken fur Osteoplastik und Osteosynthese," (63 pages), Dec. 1977.
Bunte et al., "Ceramic Augmentation of the Lower Jaw," pp. 303 to 309, Journal of Maxillofacial Surgery, vol. 5, No. 4, Dec. 1977.

*Primary Examiner*—Melvyn I. Marquis
*Attorney, Agent, or Firm*—Bacon & Thomas

[57] ABSTRACT

The composite material for prosthetic purposes of the present invention is essentially composed of a plastic matrix, preferably of a methacrylate plastic, and at least one bioactive filler material, preferably a glass ceramic material of apatite crystal structure. The finely comminuted bioactive material may be homogeneously or nonhomogeneously incorporated in the plastic matrix. Reinforcing additives such as glass fibers and the like may also be incorporated into the mixture of plastic matrix and bioactive material in order to improve the mechanical strength properties. The bioactive material may be admixed to a mixture of methacrylate monomer and curing agent or to a prepolymer obtained therefrom. The composite material is useful as bone cement, bone or tooth replacement material, and in general for prosthetic purposes in surgery and orthopedics.

23 Claims, No Drawings

BIOACTIVE COMPOSITE MATERIAL PROCESS OF PRODUCING AND METHOD OF USING SAME

CROSS-REFERENCES TO RELATED APPLICATIONS:

The present application is related to the following copending applications:

Ser. No. 471,891 of HEINZ BROEMER, HANS-HERBERT KAES, and EMANUEL PFEIL, filed May 21, 1974, now U.S. Pat. No. 3,922,155 and entitled GLASS CERAMIC MATERIAL AND PROCESS OF MAKING AND USING SAME and Ser. No. 576,797 of HEINZ BROEMER, HANS-HERBERT KAES, and EMANUEL PFEIL, filed May 12, 1975, now U.S. Pat. No. 3,981,736 and entitled GLASS CERAMIC MATERIAL AND PROCESS OF MAKING AND USING SAME, said application being a division of the aforementioned application Ser. No. 471,891. Said applications are incorporated by reference into the present specification.

BACKGROUND OF THE INVENTION (1) Field of the Invention

The present invention relates to a novel and useful bioactive composite material for prosthetic purposes, to a process of making same, and to the use of the resultant material in dental and bone surgery.

(2) Description of the Prior Art

In order to fix, i.e. firmly attach, for instance, endo-prostheses and other bone replacements in the animal or human body it is known to use a so-called "bone cement" consisting of a plastic having a base of methacrylate. For instance, in the "Zeitschrift fuer Orthopaedie" vol. 112 (1974), pages 419-426, there is described a plastic "Palakav" which contains silica gels in addition to methyl methacrylate and an organic catalyst. The ratio of methyl methacrylate to silica is 58:42 in said bone cement. The inorganic gels added to said cement serve merely as filler for the plastic matrix.

Although with the use of this composite material there have already been achieved more favorable bonding effects in the sense of a micro-meshing effect of the "Palakav" on the adjoining bone substances than with the bone cements previously used such as, for instance, "Palacos," said known bone cement is merely able to bring about a certain macro-anchoring or -meshing effect with the adjoining bone substance. It has not been possible, however, to solve with the composite materials known up to the present time the basic problem of achieving fully satisfactory anchoring or bonding between the replacement material and the bone wall in the sense of stable, chemical, principal valence-like bondings which are capable of withstanding to a substantial extent even continuous compression, tension, shear, and/or torsional stresses.

SUMMARY OF THE INVENTION

It is one object of the present invention to create a biocompatible composite material which not only has a certain "adhesiveness" but is also bioactive while avoiding the disadvantages inherent in the known materials, and thus results in a complete intergrowth at the corresponding contact surfaces between said material and the bone wall.

Another object of the present invention is to provide an appropriate method for the manufacture of a bioactive composite material in accordance with the present invention.

Still another object of the present invention is to use such a biocompatible composite material in surgery, orthopedics, and dentistry.

Other objects of the present invention and advantageous features thereof will become apparent as the description proceeds.

In principle, these objects are achieved according to the present invention by providing a composite material which consists of a plastic matrix having a base of methacrylate and of at least one bioactive material. Preferably said bioactive material is a glass ceramic material as described and claimed in U.S. Pat. No. 3,922,155 (patent application Ser. No. 471,891 mentioned hereinabove). Such a glass ceramic material with an apatite crystal phase consists, in weight percent, of about 20% to about 60% of silicon dioxide $SiO_2$,
about 5% to about 40% of phosphorus pentoxide $P_2O_5$,
about 2.7% to about 20% of sodium oxide $Na_2O$,
about 0.4% to about 20% of potassium oxide $K_2O$,
about 2.9% to about 30% of magnesium oxide $MgO$, and
about 5% to about 40% of calcium oxide $CaO$.

Such glass ceramic material may additionally contain between about 0.005% to about 3.0% of fluorine $F_2$.

A preferred glass ceramic material of this type is composed (in weight percent) of the following components:

about 30% to about 60% of silicon dioxide $SiO_2$,
about 5% to about 20% of phosphorus pentoxide $P_2O_5$,
about 3% to about 10% of sodium oxide $Na_2O$,
about 3% to about 10% of potassium oxide $K_2O$,
about 5% to about 20% of magnesium oxide $MgO$, and
about 10% to about 30% of calcium oxide $CaO$.

Such a preferred glass ceramic material may additionally contain between about 0.5% and about 2.5% of fluorine $F_2$.

Said glass ceramic material is comminuted, preferably to a particle size between about 50 $\mu m$. and about 500 $\mu m$. preferably between about 90 $\mu m$. and about 250 $\mu m$., and is added in such a finely comminuted form to the plastic matrix, wherein it is distributed either homogeneously (isotropic particle distribution) or in a precisely predetermined non-homogeneous manner (anisotropic particle distribution). Advantageously the proportion of bioactive material in the composite material is between about 10% and about 70%, by volume, and preferably between about 30% and about 60%, by volume.

It is also possible for the composite material according to the present invention to contain in addition at least one reinforcing component, preferably consisting of a fiber material, for instance, of glass fibers of known composition, in order to improve its mechanical properties.

According to an embodiment of the present invention, first there is added a pulverulent or liquid material which acts as a hardening agent, preferably an oganic peroxide, in known manner to a liquid monomeric methacrylate, preferably methyl methacrylate. Thereupon the finely comminuted bioactive glass ceramic material described hereinabove is admixed. In this connection it is of advantage, in order to achieve a precisely predetermined anisotropic particle distribution, to add the comminuted bioactive material to the mixture of methacrylate and hardener after polymerization has set in and preferably after a prepolymer of a predetermined viscosity of the mixture of methacrylate and curing agent has formed.

In accordance with a further embodiment of the present invention, a known catalyst can be added as a further additional component. Due to the strongly exothermal polymerization reaction cooling may be of advantage while proceeding in this manner. The aforesaid process steps can also take place under "in vivo" conditions, i.e. during surgical-orthopedic operations on the living organism.

In accordance with the present invention there are two important fields of application of the new bioactive composite material. First of all, it can serve as bone cement for fixing or firmly attaching artificial implants or parts of bones or teeth to the body's own bones; secondly, the completely polymerized composite material itself can be processed to prostheses or parts of prostheses which permit permanent intergrowth due to their bioactive inclusions.

The progress within a definite given period of time of the individual process steps depends on the final product desired in each case. If the composite material of the present invention is to be used as bone cement for anchoring or firmly attaching an endoprosthesis in a long hollow bone, such as a hip replacement, for instance, a finely granular fraction of the bioactive glass ceramic material is added to the liquid methyl methacrylate present in a vessel soon after the addition of the hardening agent. Said glass ceramic powder, depending on the mass of the individual pulverulent particles and the continuously increasing degree of viscosity, will penetrate and partially or completely sink into the "thickening" matrix. When polymerization has advanced to such an extent that a kneadable doughy mass results, a plastic "lump" of sufficient size for the intended purpose can be removed and can then, so to say, be covered or sprinkled with the bioactive glass ceramic powder so that said bioactive material is enriched and accumulated on the surface of the kneaded mass. The thus prepared composition is then placed as bioactive cement between the bone and the implant in accordance with its intended function.

Another possibility of preparing the composite material of the present invention to be used subsequently as bone cement consists in the feature that the plastic composition of low viscosity having admixed thereto the hardening or curing agent and a certain amount of the pulverulent bioactive material, is applied immediately "in vivo" in a thin layer on all sides, for instance, to the cylindrical inner wall of a long hollow bone, that shortly thereafter said thin layer of composite material is enriched with additional pulverized bioactive glass ceramic material, and that thereupon the main mass of the already pretreated bone cement according to the present invention is introduced.

In this way an anisotropic particle distribution of the bioactive powder which distribution is of decisive importance with respect to the chemical bonding mechanism, is specifically achieved so that the bioactive powder is accumulated at that side of the introduced cement which is facing the bone.

Selection of the particle size of the powder depends also on the specific purpose for which the composite material is to be used. It has been found that particle diameters exceeding 250 μm., do not yield optimum results due to the reduced specific surface of the embedded particles.

The duration of the preliminary polymerization to produce the workable prepolymer mixture depends upon several variable conditions such as the amount and type of hardening and curing agent added, the temperature at which prepolymerization is effected, the amounts of glass ceramic powder, polymer, either partly or completely polymerized, and other components of the mixture, the viscosity of the component mixture, and the like. These conditions can readily be determined by preliminary routine experiments depending upon the contemplated use of the final material, i.e. the bone cement or implant.

If, for instance, the composite material of the present invention itself is to be used as prosthetic material, the fluid starting material mixture of monomer, polymer, hardener, and bioactive glass ceramic material can be introduced immediately into premanufactured molds, a volume allowance (tolerance) being provided when setting up the molds because the polymer is subject to a certain amount of shrinkage which, of course, can be "mitigated" in a predetermined manner, i.e. reduced or even fully compensated for by the addition of up to 70%, by volume, of the bioactive glass ceramic material either alone or together with reinforcing fiber material. The hardened material can finally be subjected to subsequent mechanical shaping to the desired final dimensions in any desired manner such as by sawing, milling, drilling, cutting, lapping, grinding, compressing, or the like. When proceeding according to this last-mentioned example, it can be of advantage to incorporate glass fibers or other mineral fibers (whiskers, for instance, carbon fibers) in a specific manner (anisotropically) or without preferred direction (isotropically) in the same manner as with fiber-reinforced plastics.

When producing special products it is also advisable to achieve at given places of a prosthesis or part of a prosthesis an accumulation of the pulverulent bioactive particles, for instance, by segregation as a result of the force of gravity or by subsequent coating ("sprinkling").

The novel material according to the present invention can also be used in diversified fashion as filling material, for instance, for repairing locally damaged parts of bones.

Most advantageously the bioactive glass ceramic powder is first added to the polymer component of the mixture and not to the liquid monomer. When adding it to the liquid monomer or the mixture of liquid monomer and polymer, the mixture may form too viscous a matrix which cannot be mixed properly with the other components, i.e. the polymer and the hardening or curing agent. The latter agent especially when in powder form, is also preferably added to the polymer powder and the mixture of polymer powder, bioactive glass ceramic powder, and hardening or curing agent powder is admixed to the liquid monomer.

Preferred polymerizable monomers are methacrylic acid compounds, such as its esters, preferably methyl methacrylate, but also other esters, for instance, ethyl methacrylate, butyl methacrylate, isobutyl methacrylate, 2-hydroxy ethyl methacrylate, the amides of methacrylic acid, and others as they are described, for instance in Kirk-Othmer's "Encyclopedia of Chemical Technology" 2nd edition, Vol. 13, pages 331 to vol. in the chapter "Methacrylic compounds". See also the chapter on "Polymethacrylate" in the "Kunststoff-Handbuch" vol. IX, Carl Hauser Verlag, Munich 1975, pages 43 to 56. Copolymers of methacrylic acid compounds with other polymerizable monomers can, of course, also be used. Reference is also made, for instance, to the book "Zahnaerztliche Werkstoffe und ihre Verarbeitung" (in translation: Materials useful in dentistry and their processing) by Karl Eichner, published by Dr. Alfred Huethig Verlag at Heidelberg. In said book there are mentioned and disclosed plastic materials which are especially useful for producing prostheses and bone cements. Their use in dentistry is also described therein in detail. See, for instance, the chapters "6. Chemie der Kunststoffe" (in translation: Chemistry of plastic materials) pages 78–85; "8. Kunststoffverarbeitung — Theoretischer Teil" (in translation: Processing of plastic material — Theoretical section) pages 97–112; "9. Kunststoffverarbeitung – Praktischer Teil" (in translation: Processing of plastic materials — Practical section) pages 113–124; "10. Schnellhaertende Kunststoffe fuer die Prothetik" (in translation: Rapidly hardening plastic materials for prosthetic purposes) pages 126–132; "11. Weichbleibende Kunststoffe" (in translation: Plastic materials which remain soft) pages 133–143; "24. Schnellhaertende Kunststoffe" (in translation: Rapidly hardening plastic materials) pages 399–416. All the plastic materials described and used in dentistry according to the afore-mentioned book, can, of course, also be used together with the glass ceramic material according to the present invention, whereby a substantially complete growing together of the prosthesis with the bone surface is achieved.

Any suitable and conventionally used hardening or curing agents may be added. Benzoylperoxide has given excellent results, but other hardening or curing catalysts such as azobisisobutyronitrile, ammonium and other peroxysulfates, substituted benzoylperoxides, for instance, 2-chlorobenzoylperoxide, 4-methoxy benzoylperoxide, dicyclohexyl peroxydicarbonate, and other as mentioned, for instance, on page 351 of the chapter on "Methacrylic compounds" in Kirk-Othmer's "Encyclopedia of Chemical Technology" 2nd edition, vol. 13, can also be used. Curing or hardening can also be effected by irradiation as described, for instance, on page 46 of "Kunststoff-Handbuch" vol. IX.

DESCRIPTION OF THE PREFERRED EMBODIMENTS

The following examples serve to illustrate the present invention without, however, limiting the same thereto.

EXAMPLE 1

Isotropic particle distribution of the glass ceramic powder within the plastic matrix is achieved by adding said powder to the prepolymer matrix and thoroughly stirring the mixture. The resulting mixture is prepared shortly before using it, for instance, as bone cement. It hardens after application to the bone and the implant part and inserting the implant part into the bone to be repaired.

Any known acrylate plastic matrix may be used for this purpose. The following composition, for instance, has proved to be useful.

To 10 g. of polymethyl methacrylate of a molecular weight between 5000 and 6000 containing 500 mg. of benzoylperoxide there are admixed 13 g. of a glass ceramic powder of the following composition:

45.3% of silicon dioxide,
11.8% of phosphorus pentoxide,
7.5% of sodium oxide,
1.3% of potassium oxide,
3.0% of magnesium oxide,
31.0% of calcium oxide and
0.1% of fluorine as it is obtained according to the melting process described in U.S. Pat. No. 3,922,155 of HEINZ BROEMER ET AL., said powder having a particle size between about 90 $\mu$m. and about 150 $\mu$m. The mixture is added to 10.5 g. of methyl methacrylate monomer to yield a doughy mixture which is used immediately after its preparation as bone cement.

EXAMPLE 2

Anisotropic particle distribution is achieved, for instance, by providing a long, tubular, or medullated bone, inserting thereinto the shaft, shank, or stem of a conventional endoprosthesis, such as a hip joint prosthesis, and firmly and durably fixing or attaching said shaft or stem in said bone by means of the mixture of polymer having isotropically distributed therethrough the glass ceramic particles, liquid monomer, and, if required, pulverulent or liquid hardening or curing agent, said mixture serving as bone cement. Usually that part of the tubular bone into which the shaft or shank is inserted, is widened somewhat by means of a bone rasp or grater and the inner walls of the tubular bone are roughened at the same time. The roughened inner walls are provided and coated with a thin layer of the glass ceramic powder, for instance, by means of a suitable atomizer or blower which may be operated manually. The glass ceramic powder layer is preferably thin enough so that the particles adhere to the inner walls. The above mentioned three-component bone cement is then poured or pressed into the tubular bone, whereafter the shaft or stem of the endoprosthesis is introduced, pressed, force, or drilled into the bone cement and bone. The premixed bone cement continues to polymerize and is caused to fill up any non-occupied free spaces between the shaft of the endoprosthesis and the inner walls of the tubular bone. As a result of the coating of said inner walls with the glass ceramic powder there is achieved at those zones of the bone cement which face the inner bone walls a predetermined enrichment in glass ceramic powder with respect to the total concentration of the glass ceramic material in the cement, i.e. an anisotropic distribution of the particles of glass ceramic material inasmuch as the places of contact of the bone cement with the bone itself contain more particles of the bioactive material, i.e. the glass ceramic powder than the entire bone cement. Thus optimum amounts of pulverized bioactive material are supplied to those zones where bone and prosthesis are growing together. As a result thereof the physico-chemical or, respectively, crystallographic mechanism of growing together, i.e. the process of adhesion is considerably enhanced.

EXAMPLE 3

In case a prosthesis is to be attached to flat and more readily accessible places of contact of the animal or human skeleton, powdering, i.e. coating of the areas of contact between skeleton part and prosthesis can be effected by means of a simple scattering or strewing device like a salt cellar or caster.

EXAMPLE 4

The components, i.e. liquid monomer, polymer containing the finely comminuted bioactive glass ceramic material and hardening or curing agent are placed, for instance, into a cylindrical mixing vessel and are thoroughly mixed with each other. Polymerization sets in and the viscosity of the mixture increases continuousy. The glass ceramic material is isotropically distributed in the thoroughly blended mixture. On discontinuing further stirring and mixing, the glass ceramic particles start to settle due to the differences in specific gravity of the components. As a result of such settling the particles are concentrated at the bottom part of the mixing vessel. After exothermic hardening or curing of the mixture has been finished, there is obtained a cylindrically shaped body of organic composite material in which the bioactive component is anisotropically distributed in the direction of the axis of said body.

EXAMPLE 5

Anisotropic distribution of the bioactive glass ceramic component in radial direction in the mixture of liquid monomer, polymer, hardening or curing agent, and glass ceramic particles is achieved by causing the cylindrical vessel containing said mixture to rotate around its axis. By utilizing the centrifugal power exerted thereby anisotropic distribution and drifting of the glass ceramic particles into the other zones of the cylindrical body takes place.

The material obtained according to Examples 4 and 5 can be used as replacement for bones, parts of bones, and teeth. The cylindrical mixing vessel may be shaped in the form of the bone or teeth replacement, so that the polymerized product can directly be used for said purpose. Or it can be shaped mechanically as mentioned hereinabove.

The bone cement obtained according to Examples 1 to 3 can be used, as described hereinabove, for firmly attaching either artificial implant material such as artificial teeth or natural bones and parts of bones to bones of the body. Such bone cement, in proper concentration can also be used as filler material to eliminate and cover local defects in bones.

As stated hereinabove, it may become necessary to cool the place of application of the bone cement or the mold for producing bone replacement material so as to control the strongly exothermal polymerization reaction. For this purpose the place of application can be rinsed, washed, or irrigated with biocompatible, non-agressive, sterile cooling liquid. It is also possible to attach to the bone part which is in contact with the bone cement mixture according to the present invention, a cooling trap, for instance, a copper or other metal sleeve which is connected in a heat conductive manner with a cooling agent reservoir. The heat of polymerization is then conducted away from the place of application of the bone cement so that the required heat dissipation is achieved.

The term "bioactive material", as used herein and in the claims annexed hereto, indicates that the respective material is not only biocompatible, i.e. will not be rejected by the human or animal body, but also that it causes the body to attach thereto and grow theron the specific tissue, bone material, or the like of the body itself.

Of course, many changes and variations in the polymerizable monomeric material, the prepolymerized and/or polymer plastic material added to the preparation, in the hardening or curing agents and catalysts used, in the composition of the glass ceramic material and its particle size, in the manner of compounding and processing the components of the mixture, in their use as bone cement or as prosthetic material for humans and animals, and the like may be made by those skilled in the art in accordance with the principles set forth herein and in the claims annexed hereto.

We claim:

1. A composite material for prosthetic purposes, said material consisting of a polymerizable plastic matrix and between about 10 and about 70% by volume of inorganic bioactive and biocompatible material.

2. The composite material of claim 1, in which the bioactive material is a bioactive glass ceramic material having an apatite crystal phase and being of the following composition, in weight percent:

between about 20.0% and about 60.0% of silicon dioxide $SiO_2$, between about 5.0% and about 40.0% of phosphorus pentoxide $P_2O_5$, between about 2.7% and about 20.0% of sodium oxide $Na_2O$, between about 0.4% and about 20.0% of potassium oxide $K_2O$, between about 2.0% and about 30.0% of magnesium oxide MgO, and between about 5.0% and about 40.0% of calcium oxide CaO.

3. The composite material of claim 2, additionally containing between about 0.005% and about 3.0% of fluroine $F_2$.

4. The composite material of claim 1, in which the bioactive material is incorporated homogeneously in the plastic matrix so as to achieve isotropic particle distribution in said plastic matrix.

5. The composite material of claim 1, in which the bioactive material is of a particle size between about 90 $\mu$m. and 250 $\mu$m.

6. The composite material of claim 2, in which the bioactive material is of a particle size between about 90 $\mu$m. and about 250 $\mu$m.

7. The composite material of claim 3, in which the bioactive material is of a particle size between about 90 $\mu$m. and about 250 $\mu$m.

8. The composite material of claim 1, in which the bioactive material is incorporated non-homogeneously in the plastic matrix so as to achieve anistropic particle distribution in said plastic matrix.

9. The composite material of claim 1, said composite material having admixed thereto at least one reinforcing component consisting of a fiber material so as to improve its mechanical strength properties.

10. The composite material of claim 9, in which the reinforcing component consists of glass fibers.

11. The composite material of claim 1, in which the polymerizable plastic matrix is a methacrylate matrix.

12. In a process of producing the composite material of claim 1, the steps comprising a) adding a hardening agent to a fluid monomeric plastic material, and b) mixing thereto the finely comminuted bioactive glass ceramic material.

13. The process of claim 12, in which the fluid monomeric plastic material is a methacrylate plastic and the bioactive glass ceramic material is the glass ceramic material having an apatite crystal phase and being of the following composition, in weight percent:

between about 20.0% and about 60.0% of silicon dioxide $SiO_2$,
between about 5.0% and about 40.0% of phosphorus pentoxide $P_2O_5$,
between about 2.7% and about 20.0% of sodium oxide $Na_2O$,
between about 0.4% and about 20.0% of potassium oxide $K_2O$,
between about 2.0% and about 30.0% of magnesium oxide MgO, and
between about 5.0% and about 40.0% of calcium oxide CaO.

14. The process of claim 12, in which in steps (b) the finely comminuted glass ceramic material is added to a mixture of methyl methacrylate and hardening agent after prepolymerization of said mixture to a predetermined viscosity so as to achieve predetermined fractional segregation and anistropic distribution of the particles of bioactive glass ceramic material within the composite material.

15. The process of claim 12, in which a catalyst is added as additional component to the mixture of components of the composite material.

16. The process of claim 12, in which the resulting mixture is caused to polymerize completely so as to produce a prosthetic material.

17. The process of claim 12, in which the resulting mixture is applied to the bone and implant and is caused to polymerize completely "in vivo" to firmly attach the implant to the bone.

18. The process of claim 16, in which the mixture of components of the composite material is cooled during polymerization of the plastic material.

19. The process of claim 17, in which the mixture of components of the composite material is cooled during polymerization of the plastic material.

20. In a method of applying a bone cement to implants so as to firmly attach the implants to the respective skeleton parts of the body, the improvement comprising applying the bioactive composite material of claim 1 to said implants.

21. In a method of applying a bone cement to bone implants so as to firmly join the bone implants to the respective skeleton parts of the body, the improvement comprising applying the bioactive composite material of claim 1 to said implants.

22. In a method of repairing bone, the improvement comprising applying the bioactive composite material of claim 1 as a filling material.

23. In a method of using a fully polymerized material as bone or tooth prosthetic material, the improvement comprising using the fully polymerized bioactive composite material of claim 1 in the shape of bones or teeth or parts thereof.

* * * * *